United States Patent
Zheng et al.

(10) Patent No.: US 12,255,058 B2
(45) Date of Patent: *Mar. 18, 2025

(54) METHOD FOR DETERMINING DIRECTION AND DISTANCE OF METALLOGENIC PLUTON OF SKARN DEPOSIT WITH GARNET

(71) Applicants: TIBET JULONG COPPER CO., LTD., Lhasa (CN); CHINA UNIVERSITY OF GEOSCIENCES (WUHAN), Wuhan (CN)

(72) Inventors: Youye Zheng, Wuhan (CN); Xin Chen, Wuhan (CN); Xiaojia Jiang, Wuhan (CN); Feng Gao, Lhasa (CN); Shucun Wang, Lhasa (CN); Jiangang Wei, Lhasa (CN); Defu Shu, Lhasa (CN); Daohu Lin, Lhasa (CN); Zhuoga Suolang, Lhasa (CN); Jingjing Li, Lhasa (CN)

(73) Assignees: TIBET JULONG COPPER CO., LTD., Lhasa (CN); CHINA UNIVERSITY OF GEOSCIENCES (WUHAN), Wuhan (CN)

( * ) Notice: Subject to any disclaimer, the term of this patent is extended or adjusted under 35 U.S.C. 154(b) by 122 days.

This patent is subject to a terminal disclaimer.

(21) Appl. No.: 18/338,339

(22) Filed: Jun. 20, 2023

(65) Prior Publication Data

US 2024/0282565 A1     Aug. 22, 2024

(30) Foreign Application Priority Data

Feb. 20, 2023   (CN) .................... 202310181481.X (51) Int. Cl.
*H01J 49/10*     (2006.01)
*G01N 1/28*      (2006.01)
(Continued)

(52) U.S. Cl.
CPC ............ *H01J 49/105* (2013.01); *G01N 1/286* (2013.01); *G01N 33/389* (2024.05); *H01J 49/0463* (2013.01); *G01N 2001/2866* (2013.01)

(58) Field of Classification Search
CPC .. H01J 49/105; H01J 49/0463; G01N 33/389; G01N 1/286; G01N 2001/2866
See application file for complete search history.

(56) References Cited

U.S. PATENT DOCUMENTS

| | | | | |
|---|---|---|---|---|
| 9,453,829 B2* | 9/2016 | Feng | ....................... | E02D 1/025 |
| 10,451,600 B2* | 10/2019 | Sauder | ..................... | E02D 1/04 |
| 11,644,394 B2* | 5/2023 | Zhu | ........................ | G01N 1/286 |
| | | | | 73/818 |

FOREIGN PATENT DOCUMENTS

| | | | | |
|---|---|---|---|---|
| CN | 103124606 A | * | 5/2013 | ................ B22F 3/15 |
| CN | 109181643 A | * | 1/2019 | |

OTHER PUBLICATIONS

Nikoleta Tzankova "Crystal chemical features of garnets from metamorphic rocks of Zhalti Chal and UStrem Formations from the frame of Sakar pluton, SE Bulgaria", ResearchGate, pp. 531-537 (Year: 2006).*

* cited by examiner

*Primary Examiner* — Michael J Dalbo
*Assistant Examiner* — Kaleria Knox
(74) *Attorney, Agent, or Firm* — True Shepherd LLC; Andrew C. Cheng (57) ABSTRACT

A method for determining a direction and a distance of a metallogenic pluton of a skarn deposit with a garnet includes: collecting a sample; performing petrographic observation on the sample and designing an experimental area; computing a parameter; building a model; setting a parameter range; optimizing the parameters of the three (Continued)

models through a grid search method, and determining an optimal model and corresponding parameters a', b and c through repeated circulative iteration and by taking a minimum R as a limit condition; and substituting data of all sampling points into the optimal model, computing D of each sampling point, drawing a circle with a corresponding sampling point as a center and D as the radius, determining an intersection point of all circles as coordinates of the metallogenic pluton, and performing delineation with R as a buffer area of the metallogenic pluton.

6 Claims, 3 Drawing Sheets

(51) Int. Cl.
    *G01N 33/00*     (2006.01)
    *H01J 49/04*     (2006.01)

FIG. 3

METHOD FOR DETERMINING DIRECTION AND DISTANCE OF METALLOGENIC PLUTON OF SKARN DEPOSIT WITH GARNET

CROSS-REFERENCE TO RELATED APPLICATIONS

This application claims priority to Chinese Patent Application No. 202310181481.X with a filing date of Feb. 20, 2023. The content of the aforementioned application, including any intervening amendments thereto, is incorporated herein by reference.

TECHNICAL FIELD

The present disclosure belongs to the technical field of mining and particularly relates to a method for determining a direction and a distance of a metallogenic pluton of a skarn deposit with garnet.

BACKGROUND

China has rich and well-developed skarn deposits, which are the sources of valuable metal resources such as iron, copper, tungsten, tin, bismuth, molybdenum, beryllium, lead-zinc, gold, and silver. The skarn deposits are mainly found in contact zones of intermediate-acidic to intermediate-basic intrusive bodies and carbonate rocks and nearby areas. Skarn deposits dominated by iron and copper are often found near metallogenic plutons, that is, proximal skarn deposits. Skarn deposits dominated by lead and zinc are mainly found far away from metallogenic rocks and are referred to as distal skarn deposits. Numerous intermediate-acidic to intermediate-basic intrusive bodies are often developed around the proximal skarn deposits. In this case, geological mapping, alteration zoning, mineral assemblage, and geochronology are conventionally used to compare various types of plutons for determination, and determine plutons that are close to a metallogenic age and have regular alteration zoning as metallogenic plutons. However, such methods are complicated, costly and difficult to operate, and can hardly provide an accurate determination of the metallogenic pluton when there are multi-stage plutons close to the metallogenic age in an ore district. As for the distal skarn deposit, the direction and distance of the metallogenic pluton are crucial to locating the contact zone of the skarn deposit and determining a further prospecting direction. Geophysical prospecting or drilling is mainly used in existing methods to locate the metallogenic pluton of the distal skarn deposit. However, geophysical prospecting is cost-ineffective with ambiguity, and drilling is cost-ineffective and difficult to implement. In addition, it is usually impossible to locate spatially the metallogenic pluton in mining areas that have a low prospecting degree and lack pluton distribution information.

In the prior art, the ore-forming pluton of the proximal skarn deposit is mainly determined through a geological or geochemical method. A common geological method includes geological mapping, typical profile measurement, alteration zoning, mineral paragenetic association, etc. while a common geochemical method mainly includes mineral geochemistry, rock geochemistry, isotope geochemistry, etc. These methods usually require vast amounts of manpower and material resources and high cost, and it's hard to determine a pluton related to metallogeny due to unclear relations between plutons in a low operation level or coverage area.

In the prior art, the direction and distance of the metallogenic pluton of the distal skarn deposit are mainly determined through a geophysical or drilling engineering method. A common geophysical method mainly includes gravity prospecting, aeromagnetic prospecting, induced electric medium gradient profile electrical prospecting, and a common drilling engineering method includes rope coring drilling, directional drilling, air reverse circulation drilling, etc. The geophysical prospecting method is costly and demanding, features ambiguity for determining the metallogenic pluton merely based on physical parameters, and further requires the assistance of a means of dating. The drilling method is also highly costly, and cannot accurately locate the metallogenic pluton of the skarn in case of limited prospecting engineering control and sample collection.

It is urgent to develop a new and efficient mineral prospecting method for determining and locating a metallogenic pluton of a skarn deposit to quickly prospect the skarn deposit.

SUMMARY OF PRESENT INVENTION

The garnet is one of the most widely distributed minerals in a skarn deposit. It has been found that due to differences in temperature and fluid composition, spatial zoning of the garnet may occur in a skarn deposit from a pluton to a surrounding rock. It is found that the garnet will transition from grossularite to andradite in its composition during evolution from endoskarn to exoskarn. Through detailed research work, inventors have found that garnets near a metallogenic pluton are mainly grossularite, and are mainly enriched in heavy rare earth elements (HREE) and depleted in light rare earth elements (LREE); also, garnets far away from the metallogenic pluton are mainly andradite, and are mainly enriched in LREE and depleted in HREE. Therefore, a spatial variation of garnet compositions makes it possible to determine the metallogenic pluton. By building a quantitative mathematical model based on the compositions of the garnet and the distance of the metallogenic pluton, the metallogenic pluton of the skarn can be quickly and quantitatively determined and located.

The objective of the present disclosure is to take the garnet in the skarn deposit as a research object, obtain a main trace element data set with laser ablation inductively coupled plasma mass spectrometry (LA-ICPMS) analysis technology, extract trace element feature data related to the distance of the metallogenic pluton, build a mathematical model of the metallogenic pluton, build a metallogenic pluton location model of a new area by using parameter optimization methods such as enumeration and grid search in combination with features of the new area, and determine a location and a direction of a metallogenic pluton in the new area. In this way, the present disclosure can effectively solve the problems that the geological and geochemical methods have low efficiency, geophysical prospecting is of ambiguity and the drilling method is costly.

In order to achieve the above objective, the following technical solution is adopted.

A method for determining a direction and a distance of a metallogenic pluton of a skarn deposit with a garnet includes:

(1) collecting a sample:
   collecting a representative garnet sample from the skarn;
(2) performing petrographic observation on the sample and designing an experimental area:
   grinding the collected sample into a probe piece, and determining and marking a single mineral crystal area of the garnet;
(3) computing a parameter:
   obtaining a trace element content of the marked area through laser ablation inductively coupled plasma mass spectrometry (LA-ICPMS) in-situ microanalysis, and computing a ratio (L/H) of a light rare earth content to a heavy rare earth content;
(4) building a model:
   substituting the obtained ratio (L/H) of the light rare earth content to the heavy rare earth content into exponential models $D=a'(L/H)^b$ and $D=a'(L/H)^b+c$ and a logarithmic model $D=a'(\ln(L/H)+4)^{(b+0.1)}$;
(5) setting a parameter range:
   setting a parameter $a' \in [-1000,1000]$ with a step size of 50, and setting a parameter $b \in [-10,10]$ with a step size of 0.5 in the exponential model $D=a'(L/H)^b$;
   setting a parameter $a' \in [-1000,1000]$ with a step size of 50, setting a parameter $b \in [-10,10]$ with a step size of 0.5, and setting a parameter $c \in [-1000,1000]$ with a step size of 50 in the exponential model $D=a'(L/H)^b+c$; and
   setting a parameter $a' \in [-1000,1000]$ with a step size of 50, and setting a parameter $b \in [-10,10]$ with a step size of 0.5 in the logarithmic model $D=a'(\ln(L/H)+4)^{(b+0.1)}$; and
(6) optimizing parameters of the model:
   optimizing the parameters of the three models through a grid search method, and determining optimized parameters a', b and c of the three models respectively through repeated circulative iteration and by taking a minimum R as a limit condition; where R represents an optimized buffer radius:

$$R = \frac{\sum_{n}^{i=1} D'}{n} = \frac{\sum_{n}^{i=1} |(D_i - r_i)|}{n},$$

and has a threshold ≤60 m; and
   n represents the samples number, i represents a sampling point i, $D_i$ represents a linear distance in m between an optimal location of the metallogenic pluton and the sampling point i, $r_i$ represents a linear distance in m between a location of the metallogenic pluton obtained from an optimal parameter model for the sampling point i and the sampling point i, and D' represents an absolute value in m of a difference between $D_i$ and $r_i$; and
(7) locating and delineating the metallogenic pluton:
   taking a model with a minimum R among the three models as an optimal model, substituting data of all sampling points into the optimal model, computing D of each sampling point, drawing a circle with a corresponding sampling point as a center and D as the radius, determining an intersection point of all circles as coordinates (X, Y) of the metallogenic pluton, and performing delineation with R as a buffer area of the metallogenic pluton.

In one embodiment, there are no less than 5 samples in step 1, and sample information includes global positioning system (GPS) coordinate data, a field photo, lithology, alteration and a mineralization feature.

In one embodiment, in step 2, an obtained probe piece is observed under a microscope, a single mineral crystal of the garnet with a large particle size and a desirable crystal form is selected as the representative sample, and a rectangular area slightly larger than the particle size of the single mineral crystal is designed as an experimental test location and marked.

In one embodiment, step 3 includes creating a data table of a sum of a light rear earth and a heavy rare earth and the ratio (L/H) of the light rare earth content to the heavy rare earth content.

In one embodiment, step 4 of building the model includes:
   collecting a representative garnet sample from a skarn with coordinates of a metallogenic pluton known in advance;
   grinding a collected sample into a probe piece, and determining and marking a single mineral crystal area of a garnet;
   obtaining a trace element content of a marked area through LA-ICPMS in-situ microanalysis, computing the ratio (L/H) of the light rare earth content to the heavy rare earth content, and computing a distance D in meter between a sampling point and the coordinates of the metallogenic pluton; and
   obtaining the exponential models $D=a'(L/H)^b$ and $D=a'(L/H)^b+c$ by substituting the ratio (L/H) of the light rare earth content to the heavy rare earth content and the distance D into a linear model $y=bx+a$, and obtaining the logarithmic model $D=a'(\ln(L/H)+4)^{(b+0.1)}$ by substituting the ratio (L/H) of the light rare earth content to the heavy rare earth content and the distance D into a logarithmic model $y=b \ln(x)+a$.

In one embodiment, after step 6 of optimizing the model parameters, if the R is still greater than 60 m, ranges of parameters a', b and c are redefined according to the parameters a', b and c returned after iterations and the step size is reduced until R returned is less than 60 m.

Compared with the prior art, the present disclosure has the following beneficial effects:

The present disclosure provides a new mineral prospecting method for locating a metallogenic pluton of a skarn deposit with a garnet. According to the method, data analysis and parameter computation are performed on in-situ trace elements of the garnet, and a mathematical model of the metallogenic pluton and the trace elements of the garnet is built. Combined with the variability of parameters of different minerals, parameter optimization is performed on the mathematical model using the grid search method, finally, the location of the metallogenic pluton and a possible buffer area are accurately determined. This will realize a breakthrough in mineral prospecting under a condition of a low working degree or a deep edge is achieved and the method becomes an economic, efficient and simple auxiliary means and method for mineral prospecting.

Technical key points of the present disclosure are to build the mathematical model of the metallogenic pluton and the trace elements of the garnet, optimize the model through the grid search method, and build quantitative models of garnets and metallogenic plutons in different prospecting areas. The mathematical models include but are not limited to, $D=a'(L/H)^b$, $D=a'(L/H)^b+c$, and $D=a'(\ln(L/H)+4)^{(b+0.1)}$. A parameter optimization algorithm in machine learning is used to accurately locate the metallogenic pluton with R<60 m as a threshold. Key information is provided for decision-making in an early stage of prospecting, thereby creating objective economic value, and having strong guiding value for prospecting for the skarn deposit.

An orientation of a metallogenic pluton of a proximal skarn may be quickly determined in an area where the garnet exists, reducing costs by 60% or more and shortening time by 70% or longer compared with that of a traditional prospecting method. An orientation and a distance of a metallogenic pluton of a dismal skarn may be quickly located, reducing the ambiguity of the geophysical prospecting method, reducing costs by 90% or more, shortening time by 60% or longer and improving the accuracy of a target area by 50% or higher compared with that of the geophysical prospecting method and that of the drilling method. Key information for prediction may be effectively provided for mineral prospecting at the early stage or in the deep edge, thereby shortening a prospecting period and creating greater economic value.

DETAILED DESCRIPTION OF THE EMBODIMENTS

A technical solution of the present disclosure will be further explained below through embodiments, which do not limit the protection scope of the present disclosure.

A specific implementation mode provides a method for determining a direction and a distance of a metallogenic pluton of a skarn deposit with a garnet. The method includes:

(1) A representative garnet sample is collected from a skarn with coordinates of a metallogenic pluton known in advance. Longgen skarn lead-zinc deposit in Tibet is specifically selected, and at least 5 samples of garnet-bearing skarn are collected. Sampling information is recorded in Table 1.

TABLE 1

Information of Garnet Sample

| Sample No. | Sampling position | X | Y | Lithology | Occurrence | Mineral | Photo |
|---|---|---|---|---|---|---|---|
| LGGS06 |  | 136 | 52 | Garnet-bearing skarn | Massive | Garnet | ZP03 |
| LGSK-1 | TC301 | 411 | 365 | Garnet-bearing skarn | Massive | Garnet | ZP04 |
| LGSK-5 | TC501 | 283 | 223 | Garnet-bearing skarn | Vein | Garnet | ZP07 |
| ... |  | ... | ... | ... |  | ... |  |

Figure 1:
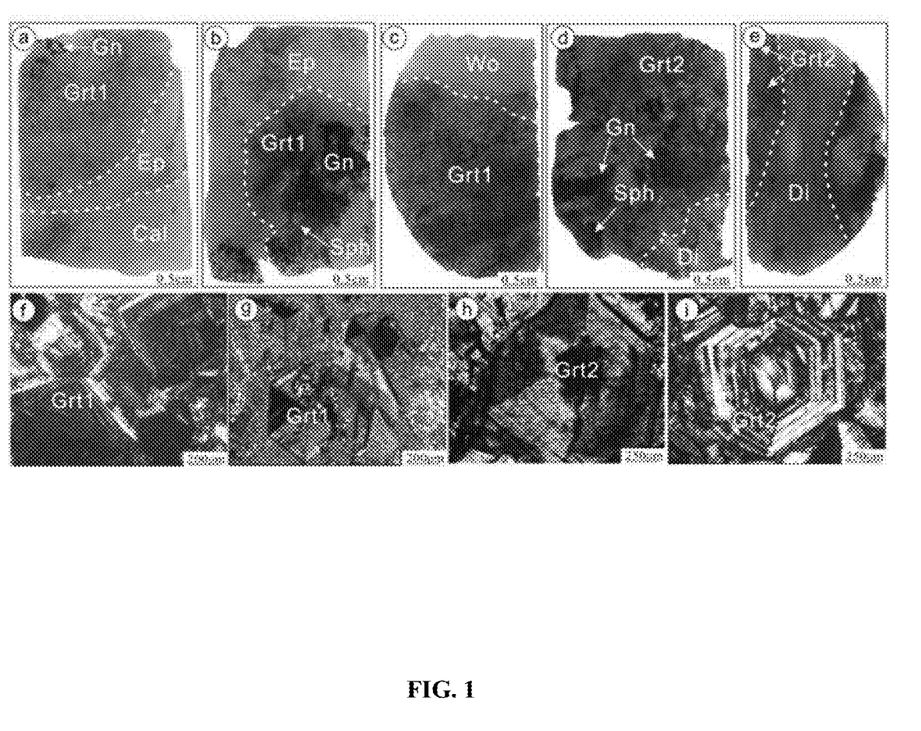
FIG. 1 shows thin-section photographs and microphotographs of garnet in Longgen skarn deposit, Tibet.

(2) The collected sample is ground into a thin section, a single mineral crystal area of the garnet is determined and marked, a feature of the garnet is observed under a microscope, a single mineral crystal with a large particle size and a desirable crystal form is selected as the representative sample, and a rectangular area slightly larger than the particle size of the single mineral crystal is designed as an experimental test location and marked by using a marking pen, as shown in FIG. 1.

(3) Laser ablation inductively coupled plasma mass spectrometry (LA-ICPMS) in-situ microanalysis is performed on a selected experimental test location, a ratio (L/H) of a light rare earth content to a heavy rare earth content is computed, and a distance D in meter between a sampling point and coordinates of the metallogenic pluton is computed, with information shown in Table 2.

TABLE 2

Computation Results

| No | La | Ce | Pr | Nd | Sm | Eu | Gd | Tb | Dy | Ho |
|---|---|---|---|---|---|---|---|---|---|---|
| 1 | 1.54 | 1.01 | 0.37 | 2.76 | 4.02 | 0.81 | 14.50 | 7.04 | 74.66 | 26.17 |
| 2 | 1.31 | 0.69 | 0.47 | 8.82 | 16.74 | 2.80 | 49.56 | 10.97 | 73.61 | 16.85 |
| 3 | 6.09 | 12.97 | 2.31 | 19.89 | 16.06 | 2.82 | 44.63 | 8.56 | 58.58 | 14.41 |
| 4 | 1.47 | 0.71 | 0.17 | 2.71 | 4.86 | 1.34 | 26.94 | 7.60 | 56.80 | 15.56 |
| 5 | 1.19 | 3.07 | 0.54 | 5.51 | 9.12 | 2.51 | 30.22 | 6.91 | 44.70 | 10.63 |
| 6 | 71.23 | 176.04 | 28.08 | 148.00 | 40.39 | 4.72 | 55.60 | 9.75 | 49.35 | 9.91 |
| 7 | 0.92 | 1.67 | 0.64 | 9.29 | 6.56 | 2.13 | 10.17 | 1.37 | 6.87 | 1.40 |
| 8 | 6.85 | 14.86 | 2.55 | 18.49 | 8.70 | 1.34 | 11.37 | 1.49 | 7.77 | 1.55 |
| 9 | 0.77 | 1.25 | 0.64 | 9.10 | 6.04 | 1.45 | 7.16 | 0.79 | 3.53 | 0.68 |
| 10 | 0.89 | 1.91 | 0.86 | 12.76 | 9.34 | 1.15 | 14.32 | 2.05 | 10.20 | 1.79 |
| 11 | 1.42 | 2.02 | 0.81 | 8.65 | 3.34 | 0.86 | 3.53 | 0.43 | 1.50 | 0.33 |
| 12 | 0.53 | 2.31 | 1.23 | 10.79 | 3.17 | 0.75 | 2.99 | 0.43 | 1.61 | 0.31 |
| 13 | 1.00 | 5.03 | 1.72 | 13.03 | 3.39 | 0.62 | 1.93 | 0.17 | 0.97 | 0.17 |

TABLE 2-continued

Computation Results

| | | | | | | | | | | |
|---|---|---|---|---|---|---|---|---|---|---|
| 14 | 0.26 | 1.48 | 0.59 | 8.15 | 6.15 | 1.32 | 9.08 | 1.22 | 5.57 | 0.93 |
| 15 | 0.53 | 2.44 | 0.70 | 4.39 | 0.87 | 0.63 | 0.87 | 0.09 | 0.16 | 0.05 |
| 16 | 0.22 | 0.20 | 0.03 | 1.06 | 2.91 | 1.32 | 12.49 | 2.61 | 17.42 | 3.68 |
| 17 | 20.82 | 50.92 | 6.76 | 28.07 | 7.76 | 1.27 | 12.19 | 1.96 | 9.27 | 1.73 |
| 18 | 0.24 | 0.23 | 0.08 | 1.63 | 2.30 | 1.43 | 11.60 | 2.21 | 12.83 | 2.72 |
| 19 | 10.63 | 20.28 | 2.26 | 6.21 | 0.27 | 0.39 | 0.27 | 0.01 | 0.00 | 0.01 |
| 20 | 1.61 | 6.14 | 1.76 | 14.14 | 6.86 | 1.41 | 10.65 | 1.42 | 7.60 | 1.26 |
| 21 | 0.30 | 2.42 | 0.71 | 5.86 | 0.76 | 0.75 | 1.24 | 0.12 | 0.46 | 0.06 |
| 22 | 0.37 | 2.14 | 0.50 | 2.04 | 0.05 | 0.40 | 0.14 | 0.00 | 0.00 | 0.00 |
| 23 | 0.60 | 2.10 | 0.46 | 3.87 | 3.10 | 1.69 | 5.09 | 0.58 | 2.83 | 0.56 |
| 24 | 0.25 | 0.40 | 0.24 | 2.66 | 2.34 | 1.50 | 1.73 | 0.24 | 0.77 | 0.14 |
| 25 | 0.92 | 1.85 | 0.40 | 3.70 | 3.31 | 2.08 | 9.65 | 1.63 | 11.33 | 2.64 |
| 26 | 0.75 | 0.46 | 0.10 | 1.29 | 1.95 | 1.54 | 4.63 | 1.12 | 7.45 | 1.71 |
| 27 | 0.95 | 1.24 | 0.22 | 1.72 | 1.97 | 1.72 | 7.35 | 1.80 | 11.75 | 2.74 |
| 28 | 1.15 | 2.94 | 1.25 | 12.15 | 3.50 | 0.57 | 2.97 | 0.34 | 1.00 | 0.17 |
| 29 | 10.08 | 27.87 | 3.45 | 11.46 | 0.80 | 0.76 | 0.50 | 0.02 | 0.09 | 0.05 |
| 30 | 11.45 | 20.41 | 1.80 | 4.69 | 0.16 | 0.08 | 0.11 | 0.07 | 0.30 | 0.03 |
| 31 | 13.48 | 30.21 | 3.34 | 7.98 | 0.89 | 0.72 | 0.47 | 0.02 | 0.06 | 0.05 |
| 32 | 9.81 | 21.76 | 2.19 | 6.11 | 0.31 | 0.13 | 0.26 | 0.05 | 0.00 | 0.03 |
| 33 | 8.97 | 31.38 | 5.16 | 19.78 | 1.84 | 0.32 | 0.69 | 0.11 | 0.27 | 0.02 |
| 34 | 8.25 | 0.00 | 1.10 | 2.98 | 0.42 | 0.05 | 0.11 | 0.01 | 0.15 | 0.02 |
| 35 | 3.51 | 4.85 | 0.52 | 1.63 | 0.10 | 0.01 | 0.05 | 0.01 | 0.06 | 0.01 |
| 36 | 4.77 | 6.55 | 0.58 | 1.52 | 0.31 | 0.01 | 0.26 | 0.02 | 0.03 | 0.01 |
| 37 | 1.51 | 0.97 | 0.05 | 0.00 | 0.20 | 0.04 | 0.10 | 0.00 | 0.03 | 0.01 |
| 38 | 2.10 | 1.58 | 0.06 | 0.16 | 0.00 | 0.03 | 0.16 | 0.00 | 0.06 | 0.00 |
| 39 | 1.97 | 1.26 | 0.06 | 0.05 | 0.00 | 0.03 | 0.05 | 0.00 | 0.00 | 0.01 |

| No | Er | Tm | Yb | Lu | REE | LREE | HREE | L/H | D |
|---|---|---|---|---|---|---|---|---|---|
| 1 | 85.44 | 12.07 | 71.32 | 7.03 | 308.72 | 10.51 | 298.22 | 0.04 | 1 |
| 2 | 43.55 | 5.60 | 26.90 | 3.63 | 261.51 | 30.83 | 230.68 | 0.13 | 3 |
| 3 | 40.03 | 4.81 | 30.97 | 4.52 | 266.65 | 60.15 | 206.51 | 0.29 | 19 |
| 4 | 46.65 | 5.80 | 35.86 | 4.40 | 210.87 | 11.26 | 199.61 | 0.06 | 2 |
| 5 | 30.14 | 3.72 | 22.53 | 3.04 | 173.84 | 21.94 | 151.90 | 0.14 | 6 |
| 6 | 23.71 | 2.10 | 11.02 | 1.42 | 631.32 | 468.47 | 162.85 | 2.88 | 44 |
| 7 | 3.71 | 0.36 | 2.09 | 0.20 | 47.37 | 21.21 | 26.16 | 0.81 | 14 |
| 8 | 2.87 | 0.39 | 1.83 | 0.26 | 80.33 | 52.79 | 27.54 | 1.92 | 49 |
| 9 | 1.30 | 0.18 | 0.82 | 0.13 | 33.84 | 19.25 | 14.59 | 1.32 | 48 |
| 10 | 3.81 | 0.55 | 1.66 | 0.28 | 61.57 | 26.92 | 34.66 | 0.78 | 20 |
| 11 | 0.86 | 0.19 | 0.47 | 0.19 | 24.61 | 17.11 | 7.50 | 2.28 | 41 |
| 12 | 0.69 | 0.05 | 0.48 | 0.20 | 25.54 | 18.78 | 6.76 | 2.78 | 41 |
| 13 | 0.34 | 0.01 | 0.63 | 0.09 | 29.10 | 24.79 | 4.31 | 5.76 | 50 |
| 14 | 2.15 | 0.13 | 1.21 | 0.26 | 38.48 | 17.94 | 20.54 | 0.87 | 15 |
| 15 | 0.16 | 0.04 | 0.24 | 0.03 | 11.19 | 9.56 | 1.63 | 5.87 | 49 |
| 16 | 8.13 | 0.98 | 6.81 | 1.14 | 59.00 | 5.73 | 53.26 | 0.11 | 3 |
| 17 | 3.70 | 0.46 | 2.40 | 0.35 | 147.66 | 115.60 | 32.05 | 3.61 | 43 |
| 18 | 6.37 | 0.77 | 5.54 | 0.94 | 48.89 | 5.90 | 42.99 | 0.14 | 4 |
| 19 | 0.04 | 0.00 | 0.06 | 0.00 | 40.44 | 40.04 | 0.39 | 101.68 | 195 |
| 20 | 2.38 | 0.26 | 2.12 | 0.35 | 57.95 | 31.91 | 26.04 | 1.23 | 50 |
| 21 | 0.07 | 0.01 | 0.09 | 0.00 | 12.84 | 10.79 | 2.05 | 5.27 | 43 |
| 22 | 0.00 | 0.00 | 0.00 | 0.00 | 5.63 | 5.49 | 0.14 | 40.58 | 157 |
| 23 | 0.96 | 0.13 | 0.68 | 0.13 | 22.77 | 11.81 | 10.96 | 1.08 | 45 |
| 24 | 0.11 | 0.04 | 0.08 | 0.01 | 10.51 | 7.39 | 3.12 | 2.37 | 40 |
| 25 | 6.91 | 1.02 | 7.62 | 1.34 | 54.39 | 12.25 | 42.14 | 0.29 | 15 |
| 26 | 5.16 | 0.72 | 5.18 | 1.07 | 33.13 | 6.09 | 27.04 | 0.23 | 10 |
| 27 | 7.82 | 0.91 | 6.78 | 1.09 | 48.07 | 7.81 | 40.26 | 0.19 | 6 |
| 28 | 0.55 | 0.04 | 0.84 | 0.21 | 27.68 | 21.56 | 6.12 | 3.52 | 112 |
| 29 | 0.07 | 0.00 | 0.29 | 0.00 | 55.44 | 54.42 | 1.02 | 53.35 | 120 |
| 30 | 0.07 | 0.01 | 0.17 | 0.03 | 39.38 | 38.59 | 0.79 | 48.85 | 108 |
| 31 | 0.04 | 0.02 | 0.24 | 0.05 | 57.57 | 56.62 | 0.95 | 59.60 | 105 |
| 32 | 0.04 | 0.00 | 0.37 | 0.06 | 41.12 | 40.31 | 0.81 | 49.77 | 145 |
| 33 | 0.05 | 0.01 | 0.45 | 0.09 | 69.14 | 67.45 | 1.69 | 39.91 | 166 |
| 34 | 0.11 | 0.04 | 0.24 | 0.04 | 13.52 | 12.80 | 0.72 | 17.78 | 179 |
| 35 | 0.07 | 0.03 | 0.10 | 0.02 | 10.97 | 10.62 | 0.35 | 30.34 | 152 |
| 36 | 0.02 | 0.00 | 0.14 | 0.03 | 14.25 | 13.74 | 0.51 | 26.94 | 169 |
| 37 | 0.02 | 0.01 | 0.00 | 0.02 | 2.96 | 2.77 | 0.19 | 14.58 | 134 |
| 38 | 0.00 | 0.00 | 0.00 | 0.00 | 4.15 | 3.93 | 0.22 | 17.86 | 200 |
| 39 | 0.00 | 0.01 | 0.00 | 0.01 | 3.45 | 3.37 | 0.08 | 42.13 | 166 |

Note:
The unit of D is meter, and the unit of elements is ppm.

Figure 2:
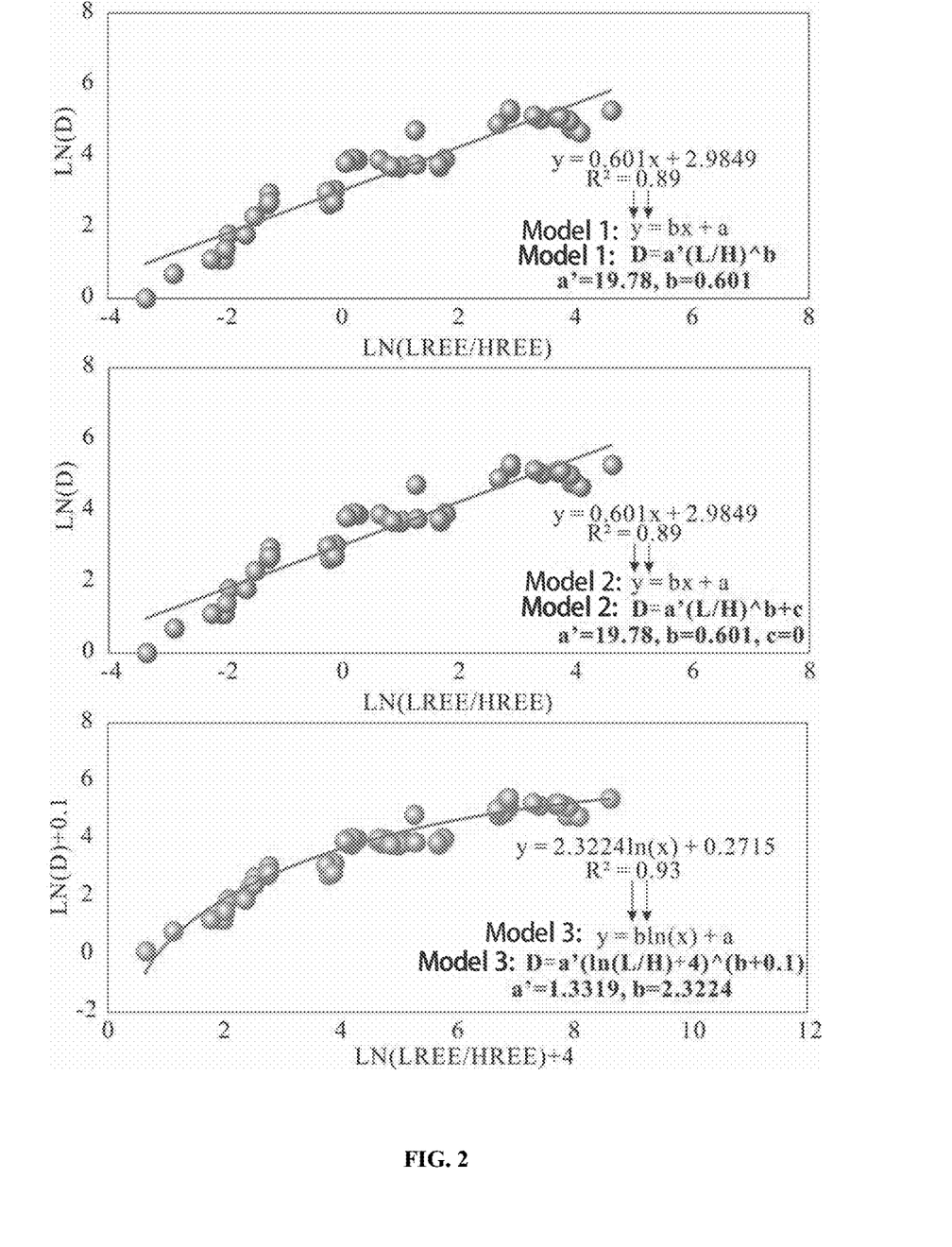
FIG. 2 shows a location model for a garnet and a metallogenic pluton of a skarn deposit in Longgen skarn deposit, Tibet.

(4) Exponential models D=a'(L/H)^b (model 1) and D=a'(L/H)^b+c (model 2) are obtained by substituting the ratio (L/H) of the light rare earth content to the heavy rare earth content and the distance D into a linear model y=bx+a, and a logarithmic model D=a'(ln(L/H)+4)^(b+0.1) (model 3) is obtained by substituting the ratio (L/H) of the light rare earth content to the heavy rare earth content and the distance D into a logarithmic model y=b ln(x)+a, as shown in FIG. 2.

A specific implementation mode further provides a method for determining a direction and a distance of a metallogenic pluton of a skarn deposit with a garnet. The method includes:

(1) A sample is collected:

a representative garnet sample is collected from the skarn.

(2) Petrographic observation is performed on the sample and an experimental area is designed:

the collected sample is ground into a thin section, and a single mineral crystal area of the garnet is determined and marked.

Figure 3:
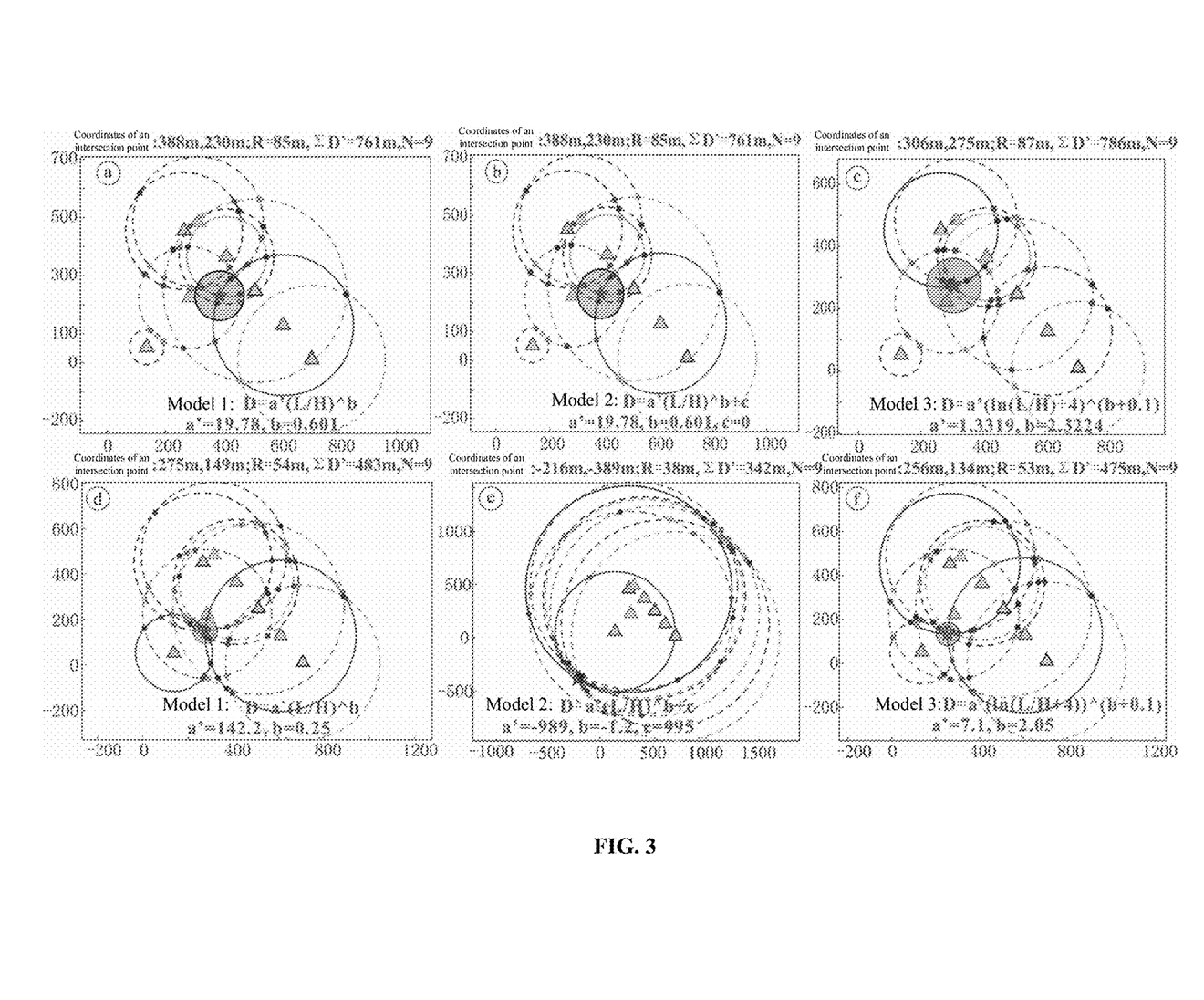
FIG. 3 shows model default parameter results (a-c) and parameter tuning optimization results (d-f).

(3) A parameter is computed:

A trace element content of the marked area is obtained through LA-ICPMS in-situ microanalysis, and a ratio (L/H) of a light rare earth content to a heavy rare earth content is computed, as shown in FIG. 3.

where R represents an optimized buffer radius:

$$R = \frac{\sum_{n}^{i=1} D'}{n} = \frac{\sum_{n}^{i=1} |(D_i - r_i)|}{n},$$

and has a threshold ≤60 m; and n represents the samples number, i represents a sampling point i, $D_i$ represents a linear distance in m between an optimal location of the metallogenic pluton and the sampling point i, $r_i$ represents a linear distance in m between a location of the metallogenic pluton obtained from an optimal parameter model for the sampling point i and the sampling point i, and D' represents an absolute value in m of a difference between $D_i$ and $r_i$.

If the R is still greater than 60 m (a-c shown in FIG. 3), ranges of parameters a', b and c are needed to be redefined according to the parameters a', b and c returned after iteration and the step size is reduced until R returned is less than 60 m (d-f shown in FIG. 3).

(7) The metallogenic pluton is located and delineated:

a model with minimum R among the three models is taken as an optimal model, data of all sampling points are substituted into the optimal model, D of each sampling point is computed, a circle is drawn with each sampling

TABLE 3

Computation Results

| No | X(m) | Y(m) | La | Ce | Pr | Nd | Sm | Eu | Gd | Tb | Dy | Ho | Er | Tm | Yb | Lu | LREE | HREE | L/H |
|---|---|---|---|---|---|---|---|---|---|---|---|---|---|---|---|---|---|---|---|
| 1 | 136.29 | 52.73 | 0.15 | 0.3 | 0.24 | 1.76 | 2.34 | 1.5 | 1.73 | 0.24 | 0.77 | 0.14 | 0.11 | 0.04 | 0.08 | 0.01 | 6.29 | 3.12 | 2.02 |
| 2 | 411.46 | 365.65 | 0.71 | 0.9 | 0.05 | 0 | 0.2 | 0.04 | 0.1 | 0 | 0.03 | 0.01 | 0.02 | 0.01 | 0 | 0.02 | 1.9 | 0.19 | 10.00 |
| 3 | 283.26 | 223.65 | 7.15 | 0 | 1.1 | 2.79 | 0.43 | 0.05 | 0.11 | 0.01 | 0.15 | 0.02 | 0.11 | 0.04 | 0.24 | 0.04 | 11.52 | 0.72 | 16.00 |
| 4 | 264.74 | 453.32 | 2.8 | 1.58 | 0.05 | 0.16 | 0 | 0.03 | 0.16 | 0 | 0.06 | 0 | 0 | 0 | 0 | 0 | 4.62 | 0.22 | 21.00 |
| 5 | 313.36 | 484.08 | 4.27 | 6.56 | 0.58 | 1.52 | 0.31 | 0.01 | 0.26 | 0.02 | 0.03 | 0.01 | 0.02 | 0 | 0.14 | 0.03 | 13.25 | 0.51 | 25.98 |
| 6 | 411.46 | 365.65 | 1.48 | 0.89 | 0.05 | 0 | 0.2 | 0.04 | 0.1 | 0 | 0.03 | 0.01 | 0.02 | 0.01 | 0 | 0.02 | 2.68 | 0.19 | 14.00 |
| 7 | 509.56 | 247.22 | 9.82 | 21.79 | 2.19 | 6.15 | 0.34 | 0.13 | 0.26 | 0.05 | 0 | 0.03 | 0.04 | 0 | 0.37 | 0.06 | 40.42 | 0.81 | 49.90 |
| 8 | 607.66 | 128.8 | 3.51 | 4.68 | 0.57 | 1.63 | 0.1 | 0.01 | 0.05 | 0.01 | 0.06 | 0.01 | 0.07 | 0.03 | 0.1 | 0.02 | 10.62 | 0.35 | 30.00 |
| 9 | 705.77 | 10.37 | 8.17 | 23.38 | 5.16 | 16.78 | 1.95 | 0.32 | 0.69 | 0.11 | 0.27 | 0.02 | 0.05 | 0.01 | 0.45 | 0.09 | 55.65 | 1.69 | 32.99 |

Note:
The unit of X and Y is meter, and the unit of elements is ppm.

(4) A model is built:

the ratio (L/H) of the light rare earth content to the heavy rare earth content obtained is substituted into exponential models D=a'(L/H)^b and D=a'(L/H)^b+c and a logarithmic model D=a'(ln(L/H)+4)^(b+0.1).

(5) A parameter range is set:

a parameter a'∈ [−1000,1000] is set with a step size of 50, and a parameter b∈ [−10,10] is set with a step size of 0.5 in the exponential model D=a'(L/H)^b;

a parameter a'∈ [−1000,1000] is set with a step size of 50, a parameter b ∈ [−10,10] is set with a step size of 0.5, and a parameter c∈ [−1000,1000] is set with a step size of 50 in the exponential model D=a'(L/H)^b+c; and a parameter a'∈ [−1000,1000] is set with a step size of 50, and a parameter b∈ [−10,10] is set with a step size of 0.5 in the logarithmic model D=a'(ln(L/H)+4)^(b+0.1).

(6) Parameters of the model are optimized:

the parameters of the three models are optimized through a grid search method, and optimized parameters a', b and c of the three models are determined respectively through repeated circulative iteration and by taking a minimum R as a limit condition;

point as a center and D as the radius, an intersection point with minimum R (38 m) of intersection points of all circles is determined as locational coordinates (X=−216 m, Y=−389 m) of the metallogenic pluton, that is, a location of a five-pointed star (e shown in FIG. 3), and delineation is performed with R (38 m) as a buffer area of the metallogenic pluton (e shown in FIG. 3).

It will be appreciated by those of ordinary skill in the art that examples herein are used for helping a reader to understand the implementation method of the present disclosure, and it should be understood that the protection scope of the present disclosure is not limited to such special statements and examples. Those of ordinary skill in the art can make other various specific modifications and combinations according to the technical teachings disclosed in the present disclosure without departing from the essence of the present disclosure.

What is claimed is:

1. A method for determining a direction and a distance of a metallogenic pluton of a skarn deposit with a garnet, comprising:

(1) collecting a sample:

collecting a representative garnet sample from the skarn;

(2) performing petrographic observation on the sample and designing an experimental area:

grinding a collected sample into a probe piece, and determining and marking a single mineral crystal area of the garnet;

(3) computing a parameter:

obtaining a trace element content of a marked area through laser ablation inductively coupled plasma mass spectrometry (LA-ICPMS) in-situ microanalysis, and computing a ratio (L/H) of a light rare earth content to a heavy rare earth content;

(4) building a model:

substituting the obtained ratio (L/H) of the light rare earth content to the heavy rare earth content into exponential models D=a'(L/H)^b and D=a'(L/H)^b+c and a logarithmic model D=a'(ln(L/H)+4)^(b+0.1);

(5) setting a parameter range:

setting a parameter a'∈[−1000,1000] with a step size of 50, and setting a parameter b∈[−10,10] with a step size of 0.5 in the exponential model D=a'(L/H)^b;

setting a parameter a'∈[−1000,1000] with a step size of 50, setting a parameter b∈[−10,10] with a step size of 0.5, and setting a parameter c∈[−1000,1000] with a step size of 50 in the exponential model D=a'(L/H)^b+c; and setting a parameter a'∈[−1000,1000] with a step size of 50, and setting a parameter b∈[−10,10] with a step size of 0.5 in the logarithmic model D=a'(ln(L/H)+4)^(b+0.1);

(6) optimizing parameters of the model:

optimizing the parameters of the three models through a grid search method, and determining optimized parameters a', b and c of the three models respectively through repeated circulative iteration and by taking a minimum R as a limit condition;

wherein R represents an optimized buffer radius:

$$R = \frac{\sum_{n}^{i=1} D'}{n} = \frac{\sum_{n}^{i=1} |(D_i - r_i)|}{n},$$

and has a threshold ≤60 m; and n represents the samples number, i represents a sampling point i, $D_i$ represents a linear distance in m between an optimal location of the metallogenic pluton and the sampling point i, $r_i$ represents a linear distance in m between a location of the metallogenic pluton obtained from an optimal parameter model for the sampling point i and the sampling point i, and D' represents an absolute value in m of a difference between $D_i$ and $r_i$; and (7) locating and delineating the metallogenic pluton:

taking a model with a minimum R among the three models as an optimal model, substituting data of all sampling points into the optimal model, computing D of each sampling point, drawing a circle with a corresponding sampling point as a center and D as the radius, determining an intersection point of all circles as coordinates (X, Y) of the metallogenic pluton, and performing delineation with R as a buffer area of the metallogenic pluton.

2. The method according to claim 1, wherein there are no less than 5 samples in step 1, and sample information comprises global positioning system (GPS) coordinate data, a field photo, lithology, alteration and a mineralization feature.

3. The method according to claim 1, wherein in step 2, an obtained probe piece is observed under a microscope, and a single mineral crystal of the garnet with a large particle size and a desirable crystal form is selected as the representative sample, and a rectangular area slightly larger than the particle size of the single mineral crystal is designed as an experimental test location and marked.

4. The method according to claim 1, wherein step 3 comprises creating a data table of a sum of a light rear earth and a heavy rare earth and the ratio (L/H) of the light rare earth content to the heavy rare earth content.

5. The method according to claim 1, wherein step 4 of building the model comprises:

collecting the representative garnet sample from the skarn with coordinates of a metallogenic pluton known in advance;

grinding the collected sample into the probe piece, and determining and marking the single mineral crystal area of the garnet;

obtaining the trace element content of the marked area through LA-ICPMS in-situ microanalysis, computing the ratio (L/H) of the light rare earth content to the heavy rare earth content, and computing a distance D in meter between a sampling point and the coordinates of the metallogenic pluton; and obtaining the exponential models D=a'(L/H)^b and D=a'(L/H)^b+c by substituting the ratio (L/H) of the light rare earth content to the heavy rare earth content and the distance D into a linear model y=bx+a, and obtaining the logarithmic model D=a'(ln(L/H)+4)^(b+0.1) by substituting the ratio (L/H) of the light rare earth content to the heavy rare earth content and the distance D into a logarithmic model y=b ln(x)+a.

6. The method according to claim 1, wherein after step 6 of optimizing the model parameters, if the R is still greater than 60 m, ranges of parameters a', b and c are redefined according to the parameters a', b and c returned after iteration and the step size is reduced until R returned is less than 60 m.

* * * * *